United States Patent
Logothetis et al.

[11] Patent Number: 5,831,145
[45] Date of Patent: Nov. 3, 1998

[54] METHOD OF INTRODUCING SELECTIVITY TO NONSELECTIVE GAS SENSORS

[75] Inventors: Eleftherios M. Logothetis, Birmingham; Michael D. Hurley, Ann Arbor; Richard E. Soltis, Saline, all of Mich.

[73] Assignee: Ford Global Technologies, Inc., Dearborn, Mich.

[21] Appl. No.: 846,993

[22] Filed: Apr. 30, 1997

[51] Int. Cl.[6] .................................................. G01N 7/00
[52] U.S. Cl. ............................................................ 73/23.2
[58] Field of Search ................................. 73/23.2, 23.31, 73/31.05, 31.06; 422/98, 94, 88; 204/425

[56] References Cited

U.S. PATENT DOCUMENTS

| | | |
|---|---|---|
| 4,399,684 | 8/1983 | Advani et al. . |
| 4,542,640 | 9/1985 | Clifford . |
| 4,627,269 | 12/1986 | Forster et al. . |
| 4,703,646 | 11/1987 | Müller et al. ............................ 73/24.01 |
| 5,027,646 | 7/1991 | Mizutani et al. ....................... 73/118.1 |
| 5,047,352 | 9/1991 | Stetter et al. ............................. 436/181 |
| 5,265,417 | 11/1993 | Visser et al. . |
| 5,451,371 | 9/1995 | Zanini-Fisher et al. . |
| 5,527,446 | 6/1996 | Kosek et al. . |
| 5,595,647 | 1/1997 | Hoetzel et al. ......................... 205/784.5 |

FOREIGN PATENT DOCUMENTS

WO 9300581   1/1993   European Pat. Off. .

*Primary Examiner*—Michael Brock
*Assistant Examiner*—Jay L. Politzer
*Attorney, Agent, or Firm*—Lorraine S. Melotik, Esq.; Roger L. May, Esq.

[57] ABSTRACT

A method of introducing selectivity to a non-selective gas sensor for determining an amount of a gas of interest contained in a measurement gas wherein the non-selective gas sensor responds not only to the gas of interest but also to other interfering gases contained in the measurement gas, the method includes the steps of periodically modulating a specified flux of a measurement gas at a first predetermined frequency, periodically modulating a specified flux of a gas of interest at a second predetermined frequency, adding the modulated flux of the gas of interest to the modulated flux of the measurement gas, exposing a non-selective gas sensor to the combination of the modulated flux of the measurement gas and the modulated flux of the gas of interest, measuring a sensor output of the non-selective gas sensor at zero frequency (DC) and at specified frequencies (AC), and determining an original concentration of the gas of interest in the measurement gas from the measured sensor output at zero frequency and at the specified frequencies.

12 Claims, 1 Drawing Sheet

METHOD OF INTRODUCING SELECTIVITY TO NONSELECTIVE GAS SENSORS

BACKGROUND OF THE INVENTION

1. Field of the Invention

The present invention relates generally to a method of introducing selectivity to a nonselective gas sensor and, more specifically, to a method for making a gas sensor respond and measure unambiguously a gas of interest x in a gas mixture containing x and other gases y based on non-linear sensor response.

2. Description of the Related Art

In recent years, gas sensors are finding an ever increasing use in many applications including combustion regulation, process control, protection against hazards, and health related applications. In the automotive industry, for example, zirconium oxide ($ZrO_2$) based oxygen sensors have been used for many years for on-board vehicle air/fuel (A/F) control and for monitoring applications. Tin oxide ($SnO_2$) based sensors are being used for detecting explosive mixtures such as methane ($CH_4$) and hydrogen ($H_2$) in air and toxic gases such as carbon monoxide (CO).

One of the main limitations of existing gas sensors is that most of them are not selective, i.e. they respond not only to the gas of interest but also to other gases. This lack of selectivity creates problems in using these gas sensors. For example, in protecting against CO poisoning, a gas sensor must be capable of responding in the 10–100 parts per million(ppm) range of CO. $SnO_2$ based sensors, however, respond not only to these CO levels but also to similar levels of other gases such as $H_2$ and $CH_4$. Consequently, a false alarm can be generated by these $SnO_2$ sensors when the ambient air contains, for example, 1000 ppm $H_2$, which presents no adverse health effect to humans. Another example for the need to have selective gas sensors, i.e., sensors responding only to a specific gas, relates to the field of automotive vehicle diagnostics. Federal and state regulations require the on-board vehicle monitoring of the efficiency of the so called Three-Way-Catalyst (TWC) in oxidizing hydrocarbons (HC). For successful use in this application, a HC gas sensor must not respond to CO because the CO concentrations in the exhaust gas of an automotive vehicle are generally considerably higher than those of the hydrocarbon.

A great deal of research and development has been expended in the last 10–20 years to improve the selectivity of existing gas sensors or to develop new more selective gas sensors. Much of this work was devoted to developing new sensing materials or modifying the properties of existing materials. For example, many modifications of $SnO_2$ have been reported either of its surface or of its bulk, e.g., by doping with a variety of ions. This approach has helped in some cases but the selectivity problem still remains. Several other methods for purporting selectivity have been reported as discussed below.

One method, currently under extensive investigation is the use of "physical" filters to separate the gaseous molecule of interest. Many materials are being developed that have controlled porosity with pores in the few Angstroms range or channels with well defined size also in the few Angstroms range. Examples of the later type of materials are the well known zeolites.

Another method is to use a "chemical" filter to remove the interfering gas before it reaches the nonselective sensor. For example, Logothetis et al. (Proc. of 2nd Intern. Meeting on Chemical Sensors, p.175, Bordeaux, France 1986) discloses a sensor for $CH_4$ which did not respond to other gases such as CO, $H_2$, alcohols, HC (e.g. alkanes) and other oxidizable gases. This sensor used a platinum (Pt) catalyst placed before a nonselective sensor such as a $SnO_2$ sensor and heated to a temperature of less than 500° C. At these temperatures, all the above-mentioned gases are catalytically oxidized and removed by the Pt catalyst except $CH_4$, that needs higher temperatures for its catalytic oxidation on Pt. Consequently, if the ambient atmosphere contains $CH_4$ and other oxidizable gases, the interfering gases are removed as they diffuse through the Pt catalyst and only $CH_4$ reaches the $SnO_2$ sensor. This method is effective but is applicable only to a few cases.

Another method which is presently under extensive study is to use an array of several nonselective gas sensors which respond to the gas of interest x and to several other gases y, but with different sensitivities. By including a sufficient number of gas sensors in the array, one can, in principle, detect the presence of molecule x in the ambient air by solving a set of equations describing the response of each sensor to the gases x and y. In practice, however, this analysis may not be unambiguous. Therefore, there is a need in the art to develop other methods for making selective sensors.

SUMMARY OF THE INVENTION

Accordingly, the present invention is a method of introducing selectivity to a non-selective gas sensor for determining the amount of a gas of interest contained in a measurement gas wherein the non-selective gas sensor responds not only to the gas of interest but also to other interfering gases contained in the measurement gas. The method includes the steps of periodically modulating a specified flux of a measurement gas at a first predetermined frequency, periodically modulating a specified flux of a gas of interest at a second predetermined frequency, and adding the modulated flux of the gas of interest to the modulated flux of the measurement gas. The method also includes exposing a non-selective gas sensor to the combination of the modulated flux of the measurement gas and the modulated flux of the gas of interest, measuring a sensor output of the non-selective gas sensor at zero frequency (DC) and at frequencies related to the first and second predetermined frequencies (AC), and determining an original concentration of the gas of interest in the measurement gas from the measured sensor output at zero frequency and at frequencies related to the first and second predetermined frequencies.

One feature of the present invention is that selectivity is provided to a non-selective gas sensor. Another feature of the present invention is that the non-selective gas sensor uses non-linear response to achieve selective gas sensing.

Other features and advantages of the present invention will be readily appreciated as the same becomes better understood after reading the subsequent description when considered in connection with the accompanying drawings.

DESCRIPTION OF THE PREFERRED EMBODIMENT(S)

Figure 1:
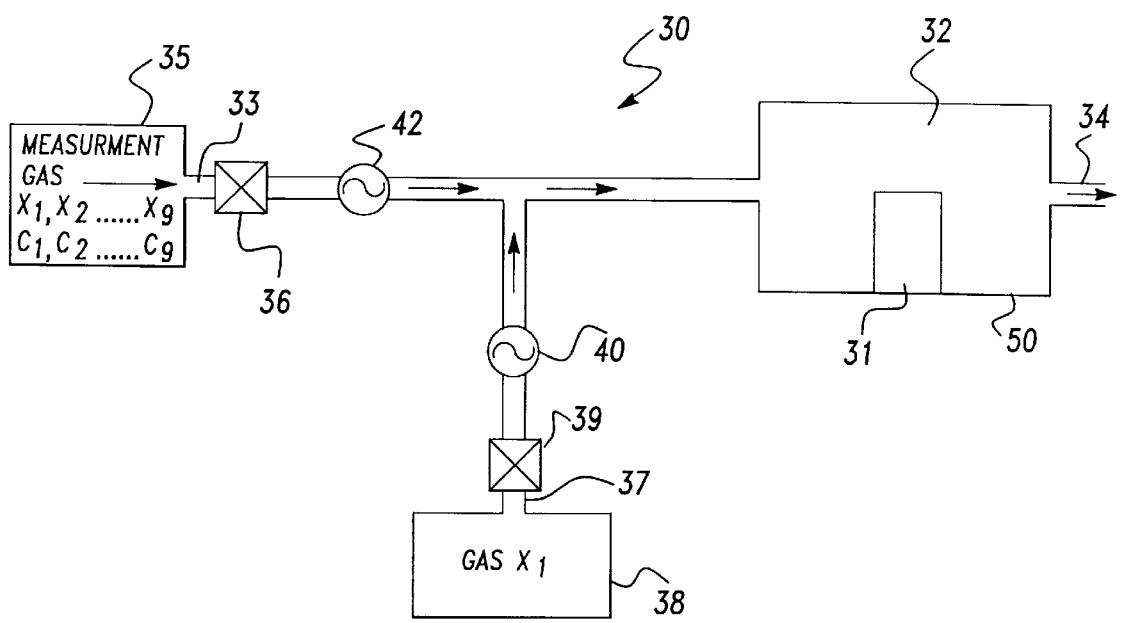
FIG. 1 is a schematic view of one embodiment used to practice a method, according to the present invention, of introducing selectivity to a non-selective gas sensor by modulating the measurement gas and by modulating the addition of a known amount of a gas of interest into the modulated measurement gas.

The present invention is directed to an apparatus and a method for determining, unambiguously, an amount of a specific gas of interest contained in a measurement gas using a non-selective sensor which responds not only to the gas of interest but also to several other interfering gases present in the measurement gas. The condition for the applicability of this method is that the non-selective sensor response is a nonlinear function of the concentration of the gas of interest. An example of such a non-selective gas sensor is the well known $SnO_2$ sensor made by Figaro Inc.

Suppose a non-selective gas sensor responds to a gas of interest $X_1$ but also to interfering gases $X_2, X_3, \ldots, X_q$, all contained in a measurement gas, according to the relationship:

$$S = f(C_1, C_2, \ldots, C_q)$$

where $C_i$ are the concentrations of gases $X_i$ in the measurement gas and $f(C_i)$ is a nonlinear function of $C_1$.

According to the present invention, a specified flux $F_0$ of the measurement gas is periodically modulated at some frequency $\omega$ before it reaches the non-selective gas sensor. A specified flux $F_1$ of the gas of interest $X_1$ is periodically modulated at some frequency $\omega$ and is added to the modulated flux $F_o$. The non-selective gas sensor response to the mixture of the two fluxes $F_o$ and $F_1$ is measured and the DC (zero frequency) and the AC (at various frequencies) components are separated by appropriate electronic circuitry conventional and known in the art. The original concentration $C_1$ of gas $X_1$ in the measurement gas is calculated from the DC and AC components of the non-selective sensor output.

One embodiment of an apparatus 30, according to the present invention, is shown in FIG. 1. The apparatus 30 includes a non-selective gas sensor 31 placed in a chamber 32 which is part of a structure 50. The structure 50 has an inlet 33 and an outlet 34 to allow a measurement gas 35 to enter the structure 50, reach gas sensor 31, and exit the structure 50. The flux $F_o$ of the measurement gas 35 entering the inlet 33 can be controlled with a flow meter 36. In another embodiment, the measurement gas 35 can be allowed to diffuse through the structure 50 with a diffusional flux defined by the geometry and dimensions of the structure 50 (including chamber 32, inlet 33, and outlet 34). The flux $F_o$ of the measurement gas 35 entering the structure 50 is time-modulated with a modulator 42. The modulator 42 can be a solenoid valve which is periodically opened and closed at some specified frequency $\omega$.

A known flux $F_1$ of a gas of interest $X_1$ is added and mixed with the flux $F_o$ of the measurement gas 35, after the modulator 42 and before the measurement gas 35 enters the chamber 32, through a second inlet 37 to the structure 50. The flux $F_1$ of gas $X_1$ is obtained from a suitable source 38, e.g. a gas cylinder containing gas $X_1$. The flux $F_1$ is controlled with a flowmeter 39 and is time-modulated with a modulator 40. The modulator 40 can be a solenoid valve which is periodically opened and closed at some chosen frequency $\acute{\omega}$ generally different from the frequency $\omega$ of the modulator 42. The output of the gas sensor 31 is measured and the DC and AC components are separated. The unknown concentration $C_1$ of gas $X_1$ in the measurement gas 35 can be then determined after the apparatus 30 is calibrated.

To illustrate how the present invention can measure, unambiguously, the concentration of the gas of interest $X_1$ when a non-selective sensor 31 is used, several examples will be discussed. It is emphasized, however, that these examples are given only for the purpose of illustration and do not impose limitations on the present invention. These examples will also demonstrate that, depending on the type of the sensor non-linearity, the modulation of both the flux of the measurement gas $F_0$ and the flux of the added gas $F_1$ is not necessary. In these cases, modulation of the flux F only without addition of $F_1$, or modulation only of the added flux $F_1$ is sufficient.

EXAMPLE 1

Consider a sensor which responds non-linearly to gas $X_1$ but linearly to gases $X_2, X_3, \ldots, X_q$, as follows:

$$S = a_1 C_1^2 + a_2 C_2 + a_3 C_3 + \ldots a_q C_q \qquad \text{Eq. (1)}$$

If the flux of the measurement gas is modulated at frequency $\omega$, the concentration of each gas $X_1, X_2, \ldots, X_q$ is also modulated. For example, if the modulation is sinusoidal and 100%, the concentration of the gases $X_1, X_2, \ldots, X_q$ in the measurement gas 35 after modulator 42 vary with time as:

$$\frac{C_1}{2}(1 - \sin\omega t), \frac{C_2}{2}(1 - \sin\omega t), \ldots, \frac{C_q}{2}(1 - \sin\omega t)$$

In this example, the addition of a modulated flux $F_1$ of gas $X_1$, is not needed. The response of the gas sensor 31 to the modulated measurement gas 35 is:

$$S = \frac{a_1 C_1^2}{4}(1 - \sin\omega t)^2 + \frac{a_2 C_2}{2}(1 - \sin\omega t) + \ldots + \frac{a_q}{2} C_q (1 - \sin\omega t) \qquad \text{Eq. (2)}$$

expanding the term $(1 - \sin\omega t)^2$ as follows:

$$(1 - \sin\omega t)^2 = 1 - 2\sin\omega t + \sin^2\omega t =$$

$$1 - 2\sin\omega t + \frac{1 - \cos 2\omega t}{2} = \frac{3}{2} - 2\sin\omega t - \frac{1}{2}\cos 2\omega t$$

S becomes:

$$S = \left[\frac{3a_1}{8} C_1^2 + \frac{a_2 C_2}{2} + \ldots + \frac{a_q}{2} Cq\right] - \qquad \text{Eq. (3)}$$

$$\left[\frac{a_1 C_1^2}{2} + \frac{a_2 C_2}{2} + \frac{a_2 C_2}{2} + \ldots + \frac{a_q}{2} C_q\right] \sin\omega t -$$

$$\frac{a_1 C_1^2}{8} \cos 2\omega t \equiv S(o) + S(\omega)\sin\omega t + S(2\omega)\cos 2\omega t$$

If the gas sensor 31 output at the frequency $2\omega$, $S(2\omega)$, is measured, the unknown concentration $C_1$ of gas $X_1$ in the measurement gas 35 can be unambiguously determined as follows:

$$S(2\omega) = \frac{a_1 C_1^2}{8} \qquad \text{Eq. (4)}$$

EXAMPLE 2

Consider again the sensor of Example 1. Instead of modulating the flux $F_0$ of the measurement gas 35, one can add into the modulated flux $F_o$ a flux $F_1$ of gas $X_1$ modulated at a frequency $\acute{\omega}$. A convenient type of modulation is simple sinusoidal modulation as follows:

$$C_{10}{}^{(1)} = C_{10} + C_{11} \sin \acute{\omega} t \qquad \text{Eq. (5)}$$

Where $C_{10}$ and $C_{11}$ are specified. The gas sensor 31 output is then given by:

$$S = a_1(C_1 + C_{10} + C_{11} \sin \acute{\omega} t)^2 + a_2 C_2 + a_3 C_3 + \ldots + a_q C_q$$

or $$S - [a_1(C_1 + C_{10})^2 + a_2C_2 + \ldots + a_qC_q] +$$  Eq. (6)

$$2_qa_1(C_1 + C_{10})C_{11}\sin\omega t + a_1C_{11}^2\sin^2\omega t =$$

$$\left[ a_1(C_1 + C_{10})^2 + a_1\frac{C_{11}^2}{2} + a_2C_2 + \ldots + a_qC_q \right] +$$

$$2_qa_1(C_1 + C_{10})C_{11}\sin\omega t - \frac{a_1C_{11}^2}{2}\cos 2\omega t \equiv S(o) +$$

$$S(\omega)\sin\omega t + S(2\omega)\cos 2\omega t$$

From the measured value $S(\omega)$, the unknown concentration $C_1$ can be determined from:

$$2a_1(C_1+C_{10})C_{11}=S(\omega)$$  Eq. (7)

EXAMPLE 3

Consider the more general sensor response function $$S=a_1C_1^{b_1}+f(C_2, C_3, \ldots, C_q)$$  Eq. (8)

where $b_1 \neq 1$ and $f(C_2, C_3, \ldots C_q)$ is a linear function of $C_2, C_3, \ldots C_q$.

As in Example 2, one can add a flux $F_1$ of gas $X_1$ modulated at frequency $\omega$ to the unmodulated flux $F_o$ of the measurement gas 35 as follows:

$$C_{10}^{(1)}=C_{10}+C_{11}\sin\omega t$$

The gas sensor 31 output is then given as:

$$S=a_1(C_1+C_{10}+C_{11}\sin\omega t)^{b_1}+f(C_2, C_3, \ldots, C_q)$$  Eq. (9)

If the assumption is made, for simplicity, that $C_{10}$ and $C_{11}$ are much smaller than $C_1$, the first term in the above expression for S can be expanded in powers of $C_{11}/C_1$ as follows:

$$S=a_1C_1^{b_1}[1+C_{10}/C_1+b\ C_{11}/C_1\sin\omega t+\ldots]+f(C_2,C_3,\ldots,C_q) \equiv S_0+S(\omega)\sin\omega t$$

Neglecting $C_0/C_1$ and keeping only the terms of zero and first order in $C_{11}/C_1$, S becomes:

$$=S_0+S(\omega)\sin\omega t$$

$$S=[a_1C_1^{b_1}+f(C_2,C_3,\ldots C_q)]+a_1b_1C_{11}C_1^{(b_1-1)}\sin\omega t$$  Eq. (10)

Consequently, the output of the gas sensor 31 consists of a DC part $S(0)$ and an AC part at frequency $\omega$, $S(\omega)$. From the measured value $S(\omega)$, the unknown concentration $C_1$ of gas $X_1$ can be determined selectively as follows:

$$C_1=[S(\omega)/(a_1b_1C_{11})]^{1/(b_1-1)}$$  Eq. (11)

EXAMPLE 4

If the gas sensor 31 responds non-linearly not only to $X_1$ but also to some of the other gases $X_2, X_3, \ldots, X_q$, then the modulation of the measurement gas 35 alone may not be sufficient for avoiding the interference of the other gases and thus being able to determine the concentration $C_1$ of gas $X_1$. For example, if the gas sensor 31 responds not according to Eq. (1) but according to the following Equation (12):

$$S=a_1C_1^2+a_2C_2^2+a_3C_3^2+\ldots+a_qC_q^2$$  Eq. (12)

Then the signal output of the sensor $S(2\omega)$ at the frequency $2\omega$ will have contributions not only from gas $X_1$ but also from all the other gases.

However, one can still measure unambiguously the concentration $C_1$ of $X_1$, by adding, as in Example 2, a flux $F_1$, of gas $X_1$ modulated at a frequency $\omega$ to the unmodulated flux $F_0$ of the measurement gas as follows:

$$C_{10}^{(1)}=C_{10}+C_{11}\sin\omega t$$

The gas sensor 31 output is now:

$$S = \left[ a_1(C_1+C_{10})^2 + a_1\frac{C_{11}^2}{2} + a_2C_2^2 + \ldots + a_qC_q^2 \right] +$$  Eq. (13)

$$2_{a_1}(C_1+C_{10})C_{11}\sin\omega t - \frac{a_1C_{11}^2}{2}\cos 2\omega t$$

The unknown concentration $C_1$ can be determined from the measurement of the component of the output at frequency $\omega$, $S(\omega)$, using the same Eq. (7).

EXAMPLE 5

Consider the non-selective gas sensor 31 which has the following response function to gases $X_1$ and $X_2$:

$$S=a_{12}C_1^nC_2^m$$  Eq. (14)

where $n \neq 1$.

If one adds the modulated flux $F_1$ of gas $X_1$ given by Eq. (5) to the flux $F_0$ of the measurement gas 35, the gas sensor 31 response is:

$$S=a_{12}(C_1+C_{10}+C_{11}\sin\omega t)^nC_2^m$$  Eq. (15)

If, for simplicity, it is assumed again that $C_{10}$ and $C_{11}$ are much smaller than $C_1$, and the same analysis as in Example 3 is used, the response of the gas sensor 31 becomes:

$$S=a_{12}C_1^nC_2^m+a_{12}nC_{11}C_1^{n-1}C_2^m\sin\omega t$$  Eq. (16)

From the measured values of the DC and AC components of the sensor 31 output $S(o)$ and $S(\omega)$, one can determine the concentration $C_1$ of gas $X_1$ as follows:

$$C_1 = nC_{11}\frac{S(o)}{S(\omega)}$$  Eq. (17)

In this example, the concentration $C_2$ of gas $X_2$ can also be determined from $S(o)$ once $C_1$ is determined.

EXAMPLE 6

Consider the gas sensor 31 of Example 5 above, but assume that the gas sensor 31 also responds to other gases $X_3, X_4, \ldots, X_q$ as follow:

$$S=a_{11}C_1^nC_2^m+f(C_3, C_4, \ldots C_q)$$  Eq. (18)

When a modulated flux of $X_1$ is added given by Eq. (5), the response of the gas sensor 31 is:

$$S=[a_{12}C_1^nC_2^m+f(C_3, C_4, \ldots, C_q)]+ a_{12}nC_{11}C_1^{n-1}C_2^m\sin\omega t$$  Eq. (19)

$$\equiv S(o)+S(\omega)\sin\omega t$$

$C_1$ is given as:

$$C_1 = nC_{11}\frac{S(o)}{S(\omega)}$$  Eq. (20)

In this example, however, $C_1$ can not be determined from Equation (20) because the ratio $S(0)/S(\omega)$ still contains the unknown concentration $C_2$ and the unknown term $f(C_2, C_4, \ldots, C_q)$.

However, even in this example, $C_1$ can be determined if one also modulates the flux $F_o$ of the measurement gas 35 at some other frequency $\omega$.

To simply the analysis, consider the case where n=2 and m=2 as follows:

$$S = a_{11}C_1^2C_2^2 + f(C_3, C_4, \ldots C_q)$$

If the flux $F_o$ of the measurement gas is modulated as in Example 1, the concentrations $C_i$ of the gases in the measurement gas 35 vary with time as:

$$\frac{C_1}{2}(1-\sin\omega t), \frac{C_2}{2}(1-\sin\omega t) \ldots, \frac{C_q}{2}(1-\sin\omega t)$$

If the added flux $F_1$ of gas $X_1$ is modulated as follows:

$$C_{10}^{(1)} = C_{10} + C_{11}\sin\acute{\omega} t$$

then the response of the gas sensor 31 to the mixture of fluxes $F_0$ and $F_1$ is:

$$S = a_{12}\left[\frac{C_1}{2}(1-\sin\omega t) + C_{10} + C_{11}\sin\acute{\omega}t\right]^2 \frac{C_2^2}{4}(1-\sin\omega t)^2 + \quad \text{Eq. (21)}$$

$$f\left(\frac{C_3}{2}(1-\sin\omega t), \ldots, \frac{C_q}{2}(1-\sin\omega t)\right)$$

After carrying out the algebra, Eq. (21) gives the following expression for the gas sensor 31 response:

$$S = \frac{a_{11}C_1^2C_2^2}{16}[L^2 - 2L(L+1)\sin\omega t + (L^2+4L+1)\sin^2\omega t - \quad \text{Eq. (22)}$$

$$2(L+1)\sin^3\omega t + \sin^4\omega t - \frac{4C_{11}}{C_1}(2L+1)\sin\omega t \cdot \sin\acute{\omega}t + \frac{4C_{11}}{C_1}L\sin\acute{\omega}t +$$

$$4\frac{C_{11}}{c_1}(L+2)\sin^2\omega t \cdot \sin\acute{\omega}t - 8\frac{C_{11}^2}{C_1}L\sin\acute{\omega}t \cdot \sin^2\omega t -$$

$$4\frac{C_{11}}{C_1}\sin^3\omega t \cdot \sin\acute{\omega}t + \frac{4C_{11}^2}{C_1^2}\sin^2\omega t \cdot \sin^2\acute{\omega}t + \frac{4C_{11}^2}{C_1^2}\sin^2\acute{\omega}t +$$

$$f\left(\frac{C_3}{2}(1-\sin\omega t), \ldots, \frac{C_q}{2}(1-\sin\omega t)\right)$$

with $L = (1 + 2C_{10}/C_1)$

The above expression shows that the gas sensor 31 output has DC components and AC components at several frequencies, $\omega$, $\acute{\omega}$, multiples of $\omega$, multiples of $\acute{\omega}$, and combinations of $\omega$ and $\acute{\omega}$. The contribution $f(C_3, \ldots, C_q)$ of the interfering gases $X_3, \ldots X_q$ can have components at DC, $\omega$, and multiples of $\omega$. Consequently, in order to calculate $C_1$, we need terms at frequencies other than 0, $\omega$, and multiples of $\omega$. For example, consider terms containing $(2\omega+\acute{\omega})$ and $(3\omega+\acute{\omega})$, the 8th term and 10th term in Eq. (22).

The 8th term is:

$$S(8th) = \frac{a_{11}C_1^2C_2^2}{16} \cdot \frac{4C_{11}}{C_1}(L+2)\sin^2\omega t \cdot \sin\acute{\omega}t$$

Using the fact that $\sin^2\omega t\cdot\sin\acute{\omega}t = \frac{1}{2}(1-\cos 2\omega t)\sin\acute{\omega}t$ and that $\cos(2\omega t)\sin\acute{\omega}t = \frac{1}{2}[\sin(2\omega+\acute{\omega})t + \sin(\acute{\omega}-2\omega)t]$.

We obtain a term at frequency $2\omega+\acute{\omega}$ as:

$$S(2\omega+\acute{\omega}) = \frac{-a_{11}C_1^2C_2^2}{16} \cdot \frac{4C_{11}}{C_1}(L+2)\left(\frac{1}{4}\sin(2\omega+\acute{\omega})t\right) = \quad \text{Eq. (23)}$$

$$\frac{-a_{11}C_1C_2^2C_{11}}{16}(L+2)\sin(2\omega+\acute{\omega})t$$

The 10th term is:

$$S(10th) = -a_{11}\frac{C_1^2C_2^2}{16} \cdot 4\frac{C_{11}}{C_1}\sin^3\omega t \cdot \sin\acute{\omega}t$$

using the fact that $$\sin^3\omega t \cdot \sin\acute{\omega}t = \frac{1}{4}(3\sin\omega t - \sin 3\omega t)\cdot\sin\acute{\omega}t$$

and that $\sin 3\omega t.\sin\acute{\omega}t = \frac{1}{2}[\cos(3\omega-\acute{\omega})t - \cos(3\omega+\acute{\omega})t]$ we obtain a term at frequency $3\omega+\acute{\omega}$ $$S(3\omega+\acute{\omega}) = \frac{-a_{11}C_1C_2^2}{4}C_{11} \cdot \frac{1}{8}\cos(3\omega+\acute{\omega})t \quad \text{Eq. (24)}$$

From Eq. (23) and Eq. (24), we can determine $C_1$ as:

$$C_1 = \frac{4C_{10}}{r-6} \quad \text{Eq. (25)}$$

where:

$$r = \frac{S(2\omega+\acute{\omega})}{S(3\omega+\acute{\omega})}$$

EXAMPLE 7

Consider again the gas sensor 31 of Example 6:

$$S = a_{11}C_1^nC_2^m + f(C_3, C_4, \ldots, C_q)$$

where n≠1.

As discussed in Example 6, if only a modulated flux $F_1$ of gas $X_1$ is added to the flux $F_0$ of the measurement gas 35, the unknown concentration $C_1$ can not be determined. However, if the response function of the gas sensor 31 to the gas $X_2$ is also nonlinear (i.e., m≠1), one can apply the modulation method also to gas $X_2$. That is, first a modulated flux $F_1$ of gas $X_1$ is added as described above to obtain a sensor response as follows:

$$S_1 = S_1(o) + S_1(\omega)\sin\omega t \quad \text{Eq. (26)}$$

with:

$$S_1(\omega) = a_{12}nC_1^{n-1}C_{11}C_2^m \quad \text{Eq. (27)}$$

Subsequently, flux $F_1$ is removed and a flux $F_2$ of gas $X_2$ is added, modulated at the same frequency $\omega$ (or at some other frequency $\acute{\omega}$), to obtain a sensor response as follows:

$$S_2 = S_2(o) + S_2(\omega)\sin\omega t \quad \text{Eq. (28)}$$

with:

$$S_2(\omega) = a_{12}mC_1^nC_2^{m-1}C_{22} \quad \text{Eq. (29)}$$

Using the measured values of $S_1(\omega)$ and $S_2(\omega)$, $C_1$ and $C_2$ can be determined from Eq. (27) and (29). It is noted that, in the above example, the two modulated fluxes $F_1$ and $F_2$ can be added together but modulated at two different frequencies $\omega$ and $\acute{\omega}$ and $C_1$ and $C_2$ can then be determined by measuring the AC sensor output components $S_1$ ($\omega$) and $S_2$ ($\acute{\omega}$) at the two frequencies $\omega$ and $\acute{\omega}$.

EXAMPLE 8

Consider a nonselective sensor which has a non-linear response not only to gas $X_1$ but also to other gases $X_2$, $X_3$, ..., $X_q$. For example:

$$S = a_1 C_1^{b_1} + a_2 C_2^{b_2} + \ldots + a_q C_q^{b_q} \qquad \text{Eq. (30)}$$

with $$b_1, b_2, \ldots, b_q \neq 1$$

It is apparent that the concentration of these gases $X_i$, if present in the measurement gas 35, can be determined by introducing modulated fluxes $F_i$ for each gas $X_i$. This can be done sequentially or at the same time provided that each flux $F_i$ is modulated at a different frequency $\omega_i$.

Examples 1 through 8 illustrate the present invention and how the present invention can be applied to some specific cases. It should be apparent that the way in which the present invention is implemented depends on the application.

It is noted that, depending on the type of non-linearity of the gas sensor response to $X_1$, the AC signal output of the gas sensor 31 may not be at the frequency $\omega$ of the modulation of the added flux $F_1$, but at some other frequency $\omega_s$ related to $\omega$ (harmonic or subharmonic). This frequency $\omega_s$ can be determined in advance during the calibration of the gas sensor 31. During the use of the gas sensor 31, the sensor output is measured at zero frequency (i.e., DC) and the frequency $\omega_s$. In more complex cases, there may be a need to measure the sensor AC components at more than one harmonic or subharmonic frequency.

In the examples of the application of the method of the present invention given above, the modulation was assumed to be sinusoidal. It should be appreciated that an exact sinusoidal modulation of the added gas (or gases) is not necessary. Other types of time-varying waveforms, e.g. square wave (on-off), could be employed.

In some of the examples discussed above, a simplification in the analysis was made by assuming that $C_{10}$ and $C_{11}$ were much smaller than $C_1$. However, the method is valid even if this assumption is not satisfied.

For the method of the present invention to be effective, the gas sensor 31 must be sufficiently fast to see the modulation in the added flux $F_1$ of gas $X_1$. If $\tau$ is the sensor response time, the frequency of modulation $\omega$ and the AC frequencies of the sensor output $\omega$, $\acute{\omega}$, $\omega_s$ defined above must all be generally smaller than $1/\tau$. In the extreme case of a very slow-responding sensor, the frequency must be very small, approaching zero; in fact, the method in this case consists of measuring (if necessary, repeatedly) the sensor response $S$ with and without the added flux $F_1$ of gas $X_1$. For the first example given by Eq. (1), the sensor output is:

$$S(\text{without added } X_1) = a_1 C_1^{b_1} + f(C_1, C_2, \ldots, C_q) \qquad \text{Eq. (31)}$$

and $$S(\text{with added } X_1) = a_1 (C_1 + C_{11})^{b_1} + f(C_1, C_2, \ldots, C_q) \qquad \text{Eq. (32)}$$

for which $C_1$ can be determined as follows:

$$C_1 = \left[ \frac{S(\text{with added } X_1) - S(\text{without added } X_1)}{a} \right]^{\frac{1}{b_1}} - C_{11} \qquad \text{Eq. (33)}$$

It is also possible that gas transport in the bulk of the measurement gas 35 or inside structure 50 is slower than the sensor response time $\tau$. In this case, the frequency of modulation should be even smaller than $1/\tau$. On the other hand, a faster gas transport may be achieved by lowering the total gas pressure.

If the presence and the concentration of gas $X_1$, in the measurement gas 35 must be monitored continuously and rapidly (within the sensor response time), the addition of the modulated flux $F_1$ of gas $X_1$ or the modulation of the incoming flux $F_o$ of the measurement gas 35 must be carried out continuously. However, this may not be necessary in all applications. For example, when gas $X_1$ and the interfering gases $X_2, X_3, \ldots, X_q$ are not normally present in the measurement gas 35, the gas sensor 31 may be operated without modulation. If at some point, the sensor output signifies the presence of one (or more) of the gases $X_1$, $X_2$, $X_3$, ..., $X_q$ in the measurement gas 35, the modulation method is employed to ascertain whether the gas of interest $X_1$ is present in the measurement gas 35 or the initial sensor signal was due to the presence of one of the interfering gases $X_2, X_3, \ldots, X_q$. This intermittent use of modulation uses the beneficial result that it conserves the added gas $X_1$. In this way, the source 38 of $X_1$ can last longer.

The use of discrete components such as conventional valves and flowmeters to construct the embodiment of FIG. 1 may result in bulky, complex, and expensive arrangements which may not be appropriate for some applications. For example, in mobile applications, e.g. automotive vehicle applications, compact and simple embodiments are highly desirable. Such embodiments can be produced by employing microfabrication techniques that are well known in the field. For example, silicon micromachining can be employed to fabricate micro-mechanical structures incorporating valves and flow controllers. This technology has made great strides in recent years and has reached the stage when it can produce complete instruments (e.g. gas chromatographs) on silicon (Si) wafers.

One constraint in the use of the method of the present invention is the need to have a source 38 for gas $X_1$. If the method is used in stationary applications, a conventional small (or large) gas cylinder containing gas $X_1$ can be used. For mobile applications, the use of a conventional gas cylinder is generally not convenient. However, when the method is employed in an embodiment based on micromachined structures, the amount of gas $X_1$ used per second can be extremely small. In this case, a miniature gas cylinder or some other miniaturized gas source could be appropriate. Such devices are well known in the field. For example, gas $X_1$ can be generated from a high surface area material where $X_1$ is stored by absorption; or it can be generated from the decomposition of a special material; or it can be generated from the reaction of very small amounts of two materials stored in the structure. It is also possible to include in the structure an active device that is able to generate the gas $X_1$; for example, an electrochemical zirconium oxide ($ZrO_2$)cell can be used to introduce into the structure oxygen ($O_2$) from the ambient air by applying an electric current with the proper polarity; or to introduce $H_2$ by the electrical decomposition of water ($H_2O$); or to introduce CO by the electrical decomposition of carbon dioxide($CO_2$). When sources of this type are used, the modulated flux $F_1$ of $X_1$ can be conveniently produced by modulating the generation of $X_1$. For example, in the case of the $ZrO_2$ cell, this can be done by applying an AC rather than a DC current through the cell (or a combination of a DC and an AC current).

Various modifications and variations will no doubt occur to those skilled in the art to which the present invention pertains. For example, the frequency (or frequencies) of modulation and the frequencies at which the sensor output is measured depends on the type of sensor used and its response to different gases and they thus vary. Modulations other than sinusoidal may also be used. More then one gas may be added in the measurement gas. The modulation methods appropriately modified, may be used even if the sensor response to the gas of interest $X_1$ is linear, provided that the sensor response to the interfering gases is nonlinear. Also the embodiment shown in FIG. 1 may be varied as to be most appropriate in a particular application.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method of introducing selectivity to a non-selective gas sensor for determining an amount of a gas of interest contained in a measurement gas wherein the non-selective gas sensor responds not only to the gas of interest but also to other interfering gases contained in the measurement gas, said method comprising the steps of:

periodically modulating a specified flux of the measurement gas at a first predetermined frequency;

periodically modulating a specified flux of the gas of interest at a second predetermined frequency;

adding the modulated flux of the gas of interest to the modulated flux of the measurement gas;

exposing the non-selective gas sensor to the combination of the modulated flux of the measurement gas and the modulated flux of the gas of interest;

measuring a sensor output of the non-selective gas sensor at zero frequency (DC) and at specified frequencies (AC); and determining an original concentration of the gas of interest in the measurement gas from the measured sensor output at zero frequency and at the specified frequencies.

2. A method of introducing selectivity to non-selective gas sensor for determining an amount of gas of interest contained in a measurement gas wherein the non-selective gas sensor responds not only to the gas of interest but also to other interfering gases contained in the measurement gas, said method comprising the steps of:

monitoring a sensor output of the non-selective gas sensor for the appearance of a signal indicating an appearance in the measurement gas of any of the gases to which the non-selective gas sensor can respond;

upon appearance of the signal, periodically modulating a specified flux of the measurement gas at a first predetermined frequency;

periodically modulating a specified flux of the gas of interest at a second predetermined frequency;

adding the modulated flux of the gas of interest to the modulated flux of the measurement gas;

exposing the non-selective gas sensor to the combination of the modulated flux of the measurement gas and the modulated flux of the gas of interest;

measuring a sensor output of the non-selective gas sensor at zero frequency (DC) and at specified frequencies (AC); and determining an original concentration of the gas of interest in the measurement gas from the measured sensor output at zero frequency and at the specified frequencies.

3. A method as set forth in claim 2 including the step of sequentially modulating the flux of each gas of interest.

4. A method as set forth in claim 3 including the step of measuring more than one gas of interest in the measurement gas.

5. A method as set forth in claim 2 including the step of concurrently modulating the flux of each gas of interest at a different frequency.

6. A method as set forth in claim 5 including the step of measuring more than one gas of interest in the measurement gas.

7. A method as set forth in claim 1 including the step of sequentially modulating the flux of each gas of interest.

8. A method as set forth in claim 7 including the step of measuring more than one gas of interest in the measurement gas.

9. A method as set forth in claim 2 including the step of concurrently modulating the flux of each gas of interest at a different frequency.

10. A method as set forth in claim 5 including the step of measuring more than one gas of interest in the measurement gas.

11. A method of introducing selectivity to a non-selective gas sensor for determining an amount of gas of interest contained in a measurement gas wherein the non-selective gas sensor responds not only to the gas of interest but also to other interfering gases contained in the measurement gas, said method comprising the steps of:

providing a specified flux of the measurement gas at a first predetermined frequency;

periodically modulating a specified flux of the gas of interest at a second predetermined frequency;

adding the modulated flux of the gas of interest to the flux of the measurement gas;

exposing the non-selective gas sensor to the combination of the flux of the measurement gas and the modulated flux of the gas of interest;

measuring a sensor output of the non-selective gas sensor at zero frequency (DC) and at specified frequencies (AC); and determining an original concentration of the gas of interest in the measurement gas from the measured sensor output at zero frequency and at the specified frequencies.

12. A method of introducing selectivity to a non-selective gas sensor for determining an amount of gas of interest contained in a measurement gas wherein the non-selective gas sensor responds not only to the gas of interest but also to other interfering gases contained in the measurement gas, said method comprising the steps of:

monitoring a sensor output of the non-selective gas sensor for the appearance of a signal indicating an appearance in the measurement gas of any of the gases to which the non-selective gas sensor can respond;

upon appearance of the signal, providing a specified flux of the measurement gas at a first predetermined frequency;

periodically modulating a specified flux of the gas of interest at a second predetermined frequency;

adding the modulated flux of the gas of interest to the flux of the measurement gas;

exposing the non-selective gas sensor to the combination of the flux of the measurement gas and modulated flux of the gas of interest;

measuring a sensor output of the non-selective gas sensor at zero frequency (DC) and at specified frequencies (AC); and determining an original concentration of the gas of interest in the measurement gas from the measured sensor output at zero frequency and at the specified frequencies.

* * * * *